United States Patent [19]

Jones, Jr. et al.

[11] 3,939,105

[45] Feb. 17, 1976

[54] MICROPOROUS POLYURETHANE HYDROGELS, METHOD AND COMPOSITES WITH NATURAL AND OTHER SYNTHETIC FIBERS OR FILMS

[75] Inventors: Allen Paul Jones, Jr., Charleston; Robert John Knopf, St. Albans; Claude Milton Conner, Nitro, all of W. Va.

[73] Assignee: Union Carbide Corporation, New York, N.Y.

[22] Filed: June 18, 1974

[21] Appl. No.: 480,567

[52] U.S. Cl.... 260/2.5 AY; 260/2.5 AD; 260/77.5 SP; 260/2.5 AP; 264/184; 428/364; 428/425
[51] Int. Cl.$^2$.......................................... C08G 18/14
[58] Field of Search... 260/2.5 AD, 2.5 AY, 77.5 SP, 260/2.5 AM; B32B/27/08; B32B/27/40

[56] References Cited
UNITED STATES PATENTS

| | | | |
|---|---|---|---|
| 3,149,000 | 9/1964 | Beicos | 260/2.5 AD |
| 3,483,015 | 12/1969 | Fukushina et al. | 260/2.5 AY |
| 3,492,154 | 1/1970 | Einstman | 260/2.5 AY |
| 3,562,374 | 2/1971 | Okamoto et al. | 260/2.5 AY |
| 3,666,542 | 5/1972 | Kigane et al. | 260/2.5 AY |
| 3,694,396 | 9/1972 | Nakahara et al. | 260/77.5 SP |
| 3,781,231 | 12/1973 | Janssen et al. | 260/2.5 AD |
| 3,789,027 | 1/1974 | Traeubel et al. | 260/2.5 AY |
| 3,821,136 | 6/1974 | Hudgin et al. | 260/2.5 AD |
| 3,822,238 | 7/1974 | Blair et al. | 260/2.5 AD |

*Primary Examiner*—H. S. Cockeram
*Attorney, Agent, or Firm*—Francis M. Fazio

[57] ABSTRACT

Microporous polyurethane hydrogels of high water swellability comprising lightly crosslinked polymers of isocyanate terminated prepolymers which are the reaction product of (i) poly(alkyleneoxy) polyol with (ii) organic diisocyanate that has been lightly crosslinked with (iii) water or an organic polyamine are produced by impregnating the isocyanato terminated prepolymer solution prior to contact with the crosslinking agent with a minor significant amount of a liquid non-solvent.

33 Claims, No Drawings

MICROPOROUS POLYURETHANE HYDROGELS, METHOD AND COMPOSITES WITH NATURAL AND OTHER SYNTHETIC FIBERS OR FILMS

BACKGROUND OF THE INVENTION

The use of various materials as absorbents for moisture is a well known, widespread practice. In this application many of the natural and synthetic materials have been used and extensive efforts have been made to improve their absorption properties. One of the major deficiencies of the natural and synthetic materials heretofore used has been the tendency for them to release the absorbed moisture when pressure has been applied to the moisture containing material. The fact that pressure causes the absorbed fluid to be expelled from the absorbent is known as reversible absorption. For many applications, however, irreversible absorption is desired, for example, in surgical dressings, diapers, bed pads, catemenials, and the like, whereby the absorbed moisture is retained in the absorbent material under an applied pressure.

Within the past few years recent innovations have resulted in the production of materials having such irreversible absorption properties; these materials are now known as hydrogels. In most instances they have been produced in powder or particulate form and even, in some instances in film form. An especially interesting characteristic of the hydrogel polymers is that when in contact with water they absorb it and swell to a certain point and stop and the final swollen polymer is still similar in shape to its initial unswollen shape. Many of the hydrogels have the ability to absorb many times their original weight in water without becoming soggy or deformed. In general, the hydrogels are used in conjunction with other materials as supports. Among the U.S. Pat. Nos. that have issued in this field are 3,699,103, 3,589,364, 3,694,301, 3,670,731, 3,164,565. This is but an exemplary listing and should not be considered complete.

SUMMARY OF THE INVENTION

Water swellable, lightly crosslinked, microporous hydrogel polymers of an isocyanato terminated prepolymer comprising the reaction product of (i) a poly(alkyleneoxy) polyol having an average molecular weight up to about 25,000 with (ii) an organic diisocyanate wherein said prepolymer is lightly crosslinked with (iii) a crosslinking agent that is water or an organic polyamine, the amount of crosslinking agent used being an equivalent amount based on the number of equivalents of isocyanato groups present in the prepolymer are produced by impregnation of the isocyanato terminated prepolymer solution with a liquid non-solvent.

DESCRIPTION OF THE INVENTION

It was recently discovered that a new class of polyurethane hydrogels could be produced by the formation of an isocyanato terminated prepolymer obtained by the reaction of poly(alkyleneoxy) polyol and organic diisocyanate followed by light crosslinking with water or an organic polyamine in which the amount of crosslinker used is sufficient to produce an essentially water insoluble hydrogel rather than the end-capped product. The fibers, films, tapes or other shaped articles were previously obtained in a substantially nonporous state. In many instances a porous product would be more desirable; it is lighter and it would have higher absorption capacity.

It has now been found that a microporous polyurethane, water swellable, lightly crosslinked, hydrogel in pellet, flake, film, tape, fiber or other configuration can be produced by impregnating the isocyanato terminated prepolymer solution with a minor significant amount of a liquid non-solvent prior to contact with the crosslinking agent. The hydrogels are the reaction products of poly(alkyleneoxy) polyol having an average molecular weight up to about 25,000 and organic diisocyanate that have been lightly crosslinked with a critical quantity of crosslinker; the crosslinker being water or an organic amine. The crosslinker can be in a coagulation bath, however, such bath is not necessary in some instances.

In accord with this invention, a liquid non-solvent is added to the isocyanato terminated prepolymer solution before it is reacted with the crosslinker. The amount of liquid non-solvent is an amount that is insufficient to cause precipitation. This amount will vary, as will become apparent, on many factors, e.g., the particular isocyanato terminated prepolymer the solvent selected, the concentration of prepolymer in the solvent, the temperature, the particular non-solvent, the degree of microporosity desired and the particular shaped item to be produced. However, it will always be a minor portion of the total of all of the solvents present in the prepolymer solution. The term "liquid non-solvent" signifies a liquid compound that is soluble in the solvent used to dissolve the isocyanato terminated prepolymer but which essentially does not dissolve the prepolymer itself and in which the hydrogel is also insoluble. The term "minor significant amount" means the amount that is insufficient to cause precipitation of the prepolymer from its solution under the particular conditions prevailing. This is generally less than 50 weight percent of the total solvent content and usually less than about 25 weight percent.

The discovery that the addition of the liquid non-solvent to the prepolymer solution before reacting the prepolymer with the crosslinker would produce a microporous hydrogel was a completely unexpected and unobvious finding.

A microporous hydrogel pellet or flake is of interest in many manufactured items. It was found that these could be produced by extruding the liquid non-solvent treated isocyanato terminated prepolymer solution, hereinafter called the impregnated solution, into the coagulation bath, through a fine capillary. The particular type of capillary used will determine whether a flake or a pellet is obtained. It was found that conventional, spinnerettes could be used to obtain flakes and that fine capillary tubes yielded pellets. To prevent agglomeration at the orifice openings, the material is extruded in a downward direction. As the impregnated solution leaves the fine capillary in droplets it enters a coagulation bath and the free isocyanato groups react with the crosslinker. The presence of the liquid non-solvent in the impregnated solution causes the hydrogel to form in a microporous state that is not obtained in the absence of the liquid non-solvent. At the same time, the prepolymer solvent is removed and the insoluble, water-swellable, lightly crosslinked hydrogel pellets and flakes are formed and conveyed away from the area below the orifice. The coagulation bath serves two purposes, it permits reaction of the isocyanato terminated prepolymer with the crosslinker and it removes the solvent from the prepolymer solution. In producing flakes or pellets one adjusts the concentration of the prepolymer in the prepolymer solution so that it will leave the capillary orifices in droplets rather than as a continuous filament or stream under the particular extrusion conditions employed with the specific composition being used.

Microporous hydrogel fibers are produced by extruding the impregnated solution through a spinnerette in continuous streams into the coagulation bath. There it is converted to the water swellable, lightly crosslinked, microporous hydrogel in the same manner as were the pellets and flakes; but the fibers are handled using conventional fiber producing techniques and equipment.

The spinning operation for producing microporous hydrogel fibers can be carried out in the manner known to those skilled in the art using spinnerettes of different hole sizes and containing different numbers of holes. The preferred method is to extrude the impregnated prepolymer solution downward into the coagulant bath to avoid blockage of the holes, then use guides to control the direction through the bath and from the bath. The solid, lightly crosslinked, microporous hydrogel fibers can be conducted over wash rolls to remove solvents and thence to drying rolls. The microporous fibers may be collected as continuous filament, tow or chopped into staple by known means; if desired, they can be subjected to a stretching treatment at any stage of the process. The equipment required and its operation in producing fibers and tapes are well known in the art.

Microporous hydrogel fibers, tapes, or ribbons are produced in the same manner as discussed above for the production of the fibers, differing only in the shape of the orifice employed, slit rather than capillary, in the extrusion.

The liquid non-solvent can be exemplified by the aliphatic hydrocarbons; preferably those boiling below about 150°C. In some instances the liquid non-solvent may be the same solvent that is used in the coagulation bath. However, while it is generally essentially the sole major solvent in the coagulation bath, it is present in the isocyanato-terminated prepolymer solution in but a minor significant amount. As suitable non-solvents one can mention hexane, heptane, octane, naphtha, nonane, decane, dipropyl ether, dibutyl ether, and the like. Trace amounts of aromatic hydrocarbons can be present. Illustrative of combinations of prepolymer solvents and liquid non-solvents are benzene/heptane, toluene/nonane, trichloroethylene/naphtha, bis2-chloroethyl ether/dibutylether, methyl ethyl ketone/-hexane, and the like.

The poly(alkyleneoxy) polyols that are used in producing the microporous hydrogel polymers of the present invention are those having a molecular weight up to about 25,000. These polyols can be diols, triols or tetrols, with the molecular weight of the polyol varying depending upon which is used.

The suitable diols are the poly(ethyleneoxy)glycols which have a molecular weight of from about 4,000 to 25,000, preferably from about 6,000 to 20,000. These diols are well known and many are commercially available. Minor amounts preferably up to about 35 weight percent of a poly(propyleneoxy) glycol or a poly(butyleneoxy) glycol can also be present. The polyols can be block or random copolymers containing mixtures of ethyleneoxy, propyleneoxy, or butyleneoxy units.

The triols and tetrols that can be used are those having a molecular weight of from about 92 to 5,000, preferably from about 500 to 1,500. These can be the poly(alkyleneoxy) polyols wherein the alkyleneoxy group contains 2 to 4 carbon atoms and they can be homopolymers or block or random copolymers having three or four reactive hydroxyl groups. One can also use the aliphatic polyhydroxyl compounds of the formula $C_nH_{2n+2-m}(OH)_m$ wherein $n$ is an integer having a value of from 3 to 6 and $m$ has a value of 3 or 4.

Illustrative of the suitable polyols are poly(ethyleneoxy) diol, poly(propyleneoxy) diol, poly(butyleneoxy) diol, copoly(ethyleneoxy-propyleneoxy) diol, poly(ethyleneoxy) triol, poly(ethyleneoxy) tetrol, poly(propyleneoxy) triol, copoly(ethyleneoxy-propyleneoxy) triol, copoly(ethyleneoxy-butyleneoxy) triol, glycerine, sorbitol, 1,2,6-hexanetriol, trimethylolpropane, pentaerythritol, dipentaerythritol, and the like. The alkyleneoxy adducts of the mono or polyamines such as ethylamine, ethanolamine, diethanolamine, ethylene diamine, propylenediamine, is opropanolamine, hexamethylene diamine, and the like. Mixtures thereof can be used if desired. In addition, one can include some polycaprolactone polyol or conventional polyester polyol.

The microporous hydrogels can be produced by reacting the poly(alkyleneoxy) diol with an organic diisocyanate to form an isocyanato terminated prepolymer which is then lightly crosslinked with a crosslinking agent that is a mixture of an organic diamine and an organic triamine. In another embodiment, the microporous hydrogels can be produced by reacting a mixture of poly(alkyleneoxy) diols and poly(alkyleneoxy) triols and/or tetrols with an organic diisocyanate to form the prepolymer which is then lightly crosslinked with a crosslinking agent that is water, an organic diamine, or a mixture thereof. When a mixture of polyols is used in producing the microporous hydrogels the mole ratio of the diol to the higher polyols is at least about 6:1 and can be as high as about 40:1. Preferably this mole ratio is from about 15:1 to about 30:1, and more preferably from about 20:1 to about 25:1. It has been observed that the mole ratio of diol to higher polyol has an effect on water uptake; the higher the mole ratio, the higher the water uptake.

Any of the known organic diisocyanates can be used in the reaction with the polyol to produce the isocyanato terminated prepolymer. These isocyanates are well known to those skilled in the polyurethane art and illustrative thereof one can mention, tolylene diisocyanate, phenylene diisocyanate, hexamethylene diisocyanate, isophorone diisocyanate, methylene bis(4-phenylisocyanate), 4,4' methylene bis(cyclohexyl isocyanate), 4,4'-methylenebis(0-tolyleneisocyanate), dimer acid diisocyanate, 4,4'-methylemebis-(phenyleneisocyanate), 2,2,4-trimethylpentane diisocyanate, aniline-formaldehyde polyisocyanates having an average of from about 2 to about 3 isocyanato groups per molecule.

In producing the isocyanato terminated prepolymer one reacts an excess of the isocyanate with the polyol. The ratio of isocyanato groups to hydroxyl is from about 1.2 to 1.6 equivalents of isocyanato per equivalent of hydroxyl. An equivalent amount of isocyanato sufficient to react with any water present in the reactants can also be added. It has been observed that at lower ratios the microporous hydrogel polymer becomes too soluble, while at ratios above 1.6:1 the water uptake of the microporous hydrogel decreases. In this reaction any of the known catalysts can be used such as dibutyltin dilaurate, stannous octoate, triethylenediamine, lead octoate, bis(dimethylamino) ethyl ether, and the like. The catalyst is present at a concentration of from about 0.001 to about one percent by weight. The conventional catalytic amounts are employed.

Production of the isocyanato terminated prepolymer is carried out in the presence of an inert organic solvent such as benzene, toluene, trichloroethane, trichloroethylene, bis(2-chloroethyl) ether, methyl ethyl ketone, ethylene dichloride, ethyl acetate, xylene, and the like.

The temperatures at which the prepolymer is produced can vary from about 50°C. to about 170°C. and is not critical to the reaction. The time required to carry the reaction the completion will vary depending upon the particular reactants and catalyst used, the size of the batch and other factors known to those skilled in the art. The reaction for the preparation of the prepolymer is preferably carried out under anhydrous conditions and under an inert gas atmosphere.

The product obtained in this first step is an isocyanato terminated prepolymer that is soluble in the organic solvent used in carrying out the reaction. This solution has a solids content dependent upon the amount of materials initially charged. For ease in further handling it is preferred that the solids content be not greater than about 40 weight percent, preferably from 10 to 35 weight percent. The solution viscosity should range from about 100 to about 200,000 centipoises.

To produce the microporous hydrogen polymer from the above isocyanato terminated prepolymer, one impregnates the solution with a liquid non-solvent and then reacts this prepolymer with a crosslinking agent to effect a light degree of crosslinking. The term "lightly crosslinked hydrogen polymer" signifies a hydrogel that contains not more than an average of about one crosslinked unit per 50,000 average molecular weight of the microporous hydrogel. Preferably there is an average of about one crosslink unit for each 100,000 to 300,000 of hydrogel molecular weight and more preferably about one crosslink unit for each 150,000 to 250,000 of hydrogel molecular weight. As previously indicated, the suitable crosslinkers are water or the organic polyamines, such as the primary or secondary diamines or triamines. The polyamines can be any of the known aliphatic or aromatic polyamines such as ethylene diamine, diethylene triamine, propylene diamines, hexamethylene diamine, methylenebis(aniline), tolylene diamine, isophorone diamine, trimethylpentane diamine, aniline-formaldehyde adduct polyamines, and the like. The amount of crosslinking agent used is an amount sufficient to react with all of the terminal isocyanato groups and to effect a light crosslinking. The desired concentration of crosslinker is that wherein the equivalents of reactive crosslinking groups in the cross-linking agent used is equivalent to the number of equivalents of isocyanato groups present in the prepolymer. This amount should be sufficient to react with all of the isocyanato groups and crosslink the polymer but it should not be an amount which would result in end-capping of the isocyanato groups rather than crosslinking.

The water swellable, lightly crosslinked, microporous hydrogels produced in this invention were found to have unexpectedly higher water absorption capacities than the materials produced by other procedures that did not employ impregnation of the isocyanato terminated prepolymer solution with liquid non-solvent prior to contact thereof with the crosslinking agent. In fact, it has been observed that the capacities can be increased as much as two-fold or more. In addition, the rate of water absorption of the microporous hydrogels of this invention is faster. The physical appearances of the microporous hydrogels is different, they are more opaque, and have a softer more pleasing hand. Further, as of this time, this impregnation process has been the only method known by which this novel type of hydrogel could be manufactured in the pellet or flake form.

The shaped microporous hydrogel articles produced by this invention can be blended with other natural and synthetic fibers, films or tapes to make composite blends. The amount of microporous hydrogel polymer in such composite can vary from 0.1 weight percent to 99.9 weight percent. This amount is dependent upon the desires of the user and how much water absorbency he wishes to impart to the finished article. Among the other materials that can be used in the blend one can mention cotton, wool, linen, flax, polyamides, polyesters, acrylics, modacrylics, acetates, celluloses, polyolefins, polyurethanes, or blends thereof.

The microporous hydrogels can be used per se or in blends in diapers, bandages, bed pads, catamenials, facial tissues and paper towels, agricultural uses, filters, and a plurality of other manufactured articles in which moisture absorbency is desired.

The following examples serve to illustrate the invention. Parts are by weight unless otherwise indicated.

EXAMPLE 1

A solution containing 1100 grams of a poly(oxyethylene) diol having an average molecular weight of about 8,500, 6.16 grams of a poly(oxyethylene) triol having an average molecular weight of about 1,190 which was the ethylene oxide adduct of glycerine and 2,694 grams of trichloroethylene solvent was heated to 86° to 89°C. while refluxing in a glass reaction vessel to remove 2.2 grams of water. The solution was then cooled to 54°C and 48.25 grams of methylenebis (4-phenylisocyanate) and 0.3462 grams of dibutyltin dilaurate were added to the kettle contents. The solution was heated and refluxed at 80°C to 88°C for 2 hours. The isocyanato to hydroxyl equivalent ratio of the solution was 1.4:1, the diol/triol molar ratio was 25.08:1 and the total solids content was 30 percent. The isocyanato equivalent weight of the resulting prepolymer solution was 45,426 with a Brookfield viscosity of 47,500 centipoises at 22°C.

A 48.1 gram portion of the isocyanato terminated prepolymer solution described above and 48.1 grams of additional trichloroethylene were mixed together to obtain a homogenous solution which contained 15 percent solids. A total of 26.42 grams of liquid non-solvent naphtha, was slowly added to the solution without causing precipitation. It was found that the addition of 1 more gram of naphtha (giving a total of 27.42 grams) did cause precipitation of the solids; however, the clear solution characteristics were restored when 1 gram of trichloroethylene was added. The amount of liquid non-solvent (naphtha) impregnation capability without precipitation for this solution was thus established as about 21.5 percent with a total solids content of 11.8 percent. A film was cast on glass and air cured utilizing ambient moisture as the crosslinking agent. This microporous hydrogel film was white, opaque (indicative of microporous structure), had good adhesion to the glass and a texture like "kid leather" or chamois. The hydrogel properties of water absorption capacity and solubility in water are compared in the following Table for films prepared from the non-impregnated and liquid non-solvent naphtha impregnated isocyanato terminated prepolymer solutions.

|  | Water Absorption Capacity (times wts. of Film) | Percent Water Soluble |
|---|---|---|
| Non-Impregnated Hydrogel Film | 20.17 | 0.66 |
| Naphtha Impregnated Microporous Hydrogel Film | 42.47 | 3.76 |

The highly significant effect of the addition of liquid non-solvent to the isocyanato terminated prepolymer solution prior to contact with the crosslinking agent is noted by the fact that the water uptake capacity was increased approximately 110 percent.

In another experiment using the liquid non-solvent naphtha impregnated isocyanato terminated prepolymer solution a portion was placed in a hypodermic syringe. The liquid non-solvent impregnated solution was extruded from the syringe in the form of droplets which were allowed to fall through an ambient air space approximately 10 to 15 inches and then into a coagulating bath containing naphtha that was 0.0001 N in ethylene diamine at room temperature. The droplets falling into the coagulating bath formed small microporous spherical pellets or beads which were found to have a water uptake capacity of 57.87 times their own weight and a water solubility of 9.93 percent.

EXAMPLE 2

An isocyanato terminated prepolymer solution was prepared as described in Example 1 at 35 percent total solids in trichloroethylene solvent. The solution had an equivalent weight of 35,503 with a Brookfield viscosity of 79,680 centipoises at 22°C. This polymer solution was divided into several portions, each of which was impregnated with various amounts of the liquid non-solvent naphtha to give impregnated solutions having a range of viscosities from 125 centipoises to 1,360 centipoises at 22°C and total solids contents which ranged from 10.4 weight percent to 15.4 weight percent.

Each of the naphtha impregnated solutions was then extruded via a conventional fiber spinning spinnerette of 30 holes, each hole 0.08 mm diameter, using a "Zenith" metering pump to supply a constant rate of 3.6 ml per minute. Droplets of the respective impregnated solutions were formed on the face of the spinnerette and were allowed to release and fall through an ambient air space of about 13 to 15 inches thence into a coagulating bath (11 inches depth) of naphtha/trichloroethylene (95/5) which contained approximately 0.0003 percent ethylene diamine as crosslinking agent. The droplets of each of the naphtha impregnated solutions were thus formed into microporous pellet or flake-like shapes and were partially dried and cured in the ambient air space with most of the solvent extraction and crosslinking occuring in the coagulating bath. The microporous pellets or flakes from each of the respective impregnated solutions were removed from the bath, dried at room temperature, and the water absorption capacities and water solubilities were determined. The results of these experiments are shown in the following Table:

TABLE

| Run | Solids Content After Dilution and Impregnation (%) | Non-Solvent Solvent Percent | Absorption Water Capacity | % Water Solubilities |
|---|---|---|---|---|
| 1 | 15.40 | 14.2/85.8 | 23.88 | 2.69 |
| 2 | 14.19 | 16.4/83.6 | 30.59 | 2.25 |
| 3 | 13.00 | 18.6/81.4 | 40.23 | 3.43 |
| 4 | 11.48 | 20.3/79.7 | 42.89 | 6.03 |
| 5 | 10.94 | 21.3/78.7 | 42.95 | 5.38 |
| 6 | 10.40 | 22.3/77.7 | 44.59 | 4.04 |

The effects of the non-solvent impregnation of the isocyanate terminated prepolymer solution at the various solids and viscosity levels shown in the Table were as follows: Pellets or flakes produced from the naphtha impregnated solutions 4 to 6 were the most uniform in size and shape, being circular and flake-like, and they had the highest water absorption capacities which increased with the amount of liquid non-solvent impregnant used. The microporous hydrogel pellets or flakes which were produced from solutions 1 to 3 were more irregular in size and shape being somewhat spherical, with an increasing amount of fines and filamentary material noted at the higher solids, lower impregnation levels.

EXAMPLE 3

Naphtha impregnated isocyanato terminated prepolymer solutions 4 and 5 from Example 2 were extruded via a 20 holes spinnerette, each hole 0.09 mm diameter, at a pumping rate of 1.5 grams of prepolymer solids per hour per hole. The procedure was much the same as described in Example 2 except that the droplets of prepolymer were extruded into an ambient air space (15") encircled by a "glass" tube, to provide protection from room air currents, and thence into a coagulating or crosslinking bath containing 95 percent naphtha/5 percent trichloroethylene, that was 0.0001 N in ethylene diamine. The impregnated microporous hydrogel pellets or flakes passed a distance of about 4 to 5 inches in the coagulating bath onto a mesh conveyor belt and were carried about 55 inches through the bath and collected in a wire basket at the end of the conveyor belt. The microporous hydrogel particles were dried at room temperature and their properties determined.

| Run | 4 | 5 |
|---|---|---|
| Particle Dimensions, avg. |  |  |
| Diameter, Inch | ⅛ | ⅛ |
| Thickness, Inch | 1/32 | 1/32 |
| Water Absorption Capacity | 52 fold | 51 fold |
| Water Solubility, Percent | 1.5 | 1.2 |

EXAMPLE 4

An isocyanato terminated prepolymer solution was prepared as described in Example 1, at 30 percent solids content then further reduced to 25.2 percent solids by addition of trichloroethylene solvent. This prepolymer solution had an equivalent weight of 62,939 and a Brookfield viscosity of 10,000 centipoise at 22°C. A portion of this prepolymer solution was then further reduced to 10 percent solids content by addition of an 80/20 mixture of trichloroethylene and naphtha, using the naphtha as the liquid non-solvent. This low viscosity (100 cps) naphtha impregnated prepolymer solution was then placed in a conventional pressure type air actuated paint spray gun. Two samaples of non-woven structures (batts) were produced, the first by spraying the impregnated prepolymer solution into ambient air and letting the filaments thus formed fall into a coagulating bath containing naphtha/trichloroethylene (95/5) that was 0.0001 N in ethylene diamine; the second sample was sprayed into air, thence onto "nonsticking" cloth, using atmospheric moisture as the crosslinker. The first non-woven batt had a finer weave than the second batt. The properties of the microporous hydrogel batts were obtained and are given below.

|  | Water Absorption Capacity | Percent Water Soluble |
|---|---|---|
| Film (Cast on glass and air cured) | 30.01 fold | 0.91 |
| First Non-woven Batt | 40.03 fold | 7.33 |
| Second Non-woven Batt | 32.85 fold | 15.31 |

EXAMPLE 5

An isocyanato terminated prepolymer solution was prepared by heating 1125 grams of the poly(oxyethylene) diol and 5.58 grams of the poly(oxyethylene) triol used in Example 1 in 2,401 grams of trichloroethylene solvent at 76°C to 90°C while refluxing to remove 3.6 grams of water. The heat was removed, allowing the kettle contents to cool to 75° to 78°C, and 51.84 grams of methylenebis (4-phenylisocyanate) and 0.3547 gram of dibutyltin dilaurate were added. The solution was heated and refluxed at 75° to 89°C for two hours. The isocyanato to hydroxy equivalent ratio of the prepolymer solution was 1.4:1, the diol to triol molar ratio was 30:1 and the total solids content was 33 percent. At this point 354 grams of the liquid non-solvent naphtha was added to the prepolymer solution and the solids content was reduced to about 30 percent. The equivalent weight of the resulting impregnated prepolymer solution was 36,306 and the Brookfield viscosity was 67,360 at 22°C.

The naphtha impregnated isocyanato terminated prepolymer solution was extruded via a slit-type die having an opening 3 inches by 0.007 inches to form a continuous microporous hydrogel tape using a Zenith metering pump to supply a constant rate of 19 ml per minute. To produce this tape the slit-type die was positioned vertically approximately ½-inch to 1 inch above the surface of a coagulating bath which contained naphtha and trichloroethylene (95/5) that was 0.0001 N in ethylene diamine at a temperature of 22°C.

The impregnated prepolymer solution was thus extruded from the slit die in a ribbon-like fluid gel state and passed initially through the ½ to 1 inch ambient air space and thence vertically downward into the coagulating and crosslinking bath and onto a conveyor belt running 4 to 5 inches below the bath surface. The impregnated prepolymer solution coagulated rapidly and did not adhere to the belt. The microporous hydrogel tape was carried through the coagulating bath approximately 55 inches at rates of 8 and 12 feet per minute, drawn over a series of drying rolls heated at 30° to 40°C at rates of 10 and 14 feet per minute and then collected on a package using a surface drive take-up at rates of about 11 and 15 feet per minute. The tape samples thus obtained were about 1 inch wide by 0.0006 inch thick and opaque with good appearance. The properties of the microporous hydrogel tape along with a film cast from the same non-impregnated prepolymer solution on glass and air cured for comparison purposes are set forth below.

|  | Water Absorption Capacity | Percent Water Solubles |
|---|---|---|
| Film cast on glass and air cured | 23.36 fold | 0.7 |
| Impregnated hydrogel tape (8 ft. per min.) | 31.42 fold | 3.97 |
| Impregnated hydrogel tape (12 ft. per min.) | 32.22 fold | 6.22 |

EXAMPLE 6

An isocyanato terminated prepolymer solution was prepared as described in Example 1 except the isocyanato to hydroxyl equivalent ratio was 1.325:1, the diol to triol molar ratio was 22.5:1 and the total solids content was initially 35 percent. Sufficient naphtha was added as the liquid non-solvent impregnant to reduce this to 34.1 percent. This impregnated prepolymer solution was transferred from the reaction vessel to a stainless steel dope pot under nitrogen. The solution was then extruded through spinnerettes to form multifilament yarns by the conventional spinning procedures. The spinnerettes were positioned about 10 to 15 inches above the coagulating bath and the filaments were extruded vertically downward into ambient air thence into the bath containing naphthatrichloroethylene (95/5) that was 0.0001 N in ethylene diamine. The filaments were drawn downward through the bath 6 to 8 inches then horizontally about 12 inches and vertically upward about 6 to 8 inches passing through a wash bath containing naphtha for a distance of approximately 12 to 14 inches. The microporous hydrogel fibers then were drawn over drying rolls and dried at 30°C. The filaments were then packaged at about 30 fpm. The impregnated microporous hydrogel fibers were opaque, had a soft hand, were insoluble in trichloroethylene, slightly elastomeric and of good appearance. Fiber samples were obtained with spinnerettes of 40 holes, 60 holes and 100 holes, each hole 0.1mm in diameter. These fibers all had elongations at break of over 100 percent and the following properties:

| Number of Filaments | Denier | Denier Per Filament | Water Absorption Capacity | Percent Water Soluble |
|---|---|---|---|---|
| 40 | 200 | 5 | 21.2 fold | 1.30 |
| 60 | 1054 | 17.6 | 21.6 fold | 1.39 |
| 100 | 951 | 9.5 | 21.2 fold | 1.21 |

What we claim is:

1. An article of manufacture comprising a composite of (I) a shaped microporous, water swellable, lightly crosslinked, hydrogel polymer article of the isocyanato terminated prepolymer comprising the reaction product of:

i. a poly(alkyleneoxy) polyol having an average molecular weight up to about 25,000 wherein the alkyleneoxy group contains from 2 to 4 carbon atoms, and ii. an organic diisocyanate, said prepolymer impregnated with a minor significant amount of a liquid non-solvent prior to lightly crosslinking thereof with an equivalent amount of a crosslinking agent of the group:

iii. water or organic polyamine; wherein said poly(alkyleneoxy) polyol is a mixture of a major amount of a poly(ethyleneoxy) diol having an average molecular weight of from about 4,000 to about 25,000 and a minor amount of a higher polyol of the group poly(alkyleneoxy) triol or poly(alkyleneoxy) tetrol having from 2 to 4 carbon atoms in the alkyleneoxy group or aliphatic polyhydroxyl compound of the formula $C_nH_{2n+2-m}(OH)_m$ wherein n has a value of 3 to 6 and m has a value of 3 to 4, or mixtures thereof, said triol or tetrol having an average molecular weight of from about 92 to 5,000, wherein the mole ratio of diol to higher polyol in said mixture is from about 6:1 to 40:1; wherein the equivalents ratio of isocyanato groups to hydroxyl groups is from about 1.2:1 to about 1.6:1; wherein the organic polyamine is a primary or secondary diamine or triamine and wherein the equivalents of reactive crosslinking groups in said crosslinking agent used is equivalent to the number of equivalents of isocyanato groups present in said prepolymer; in combination with (II) a natural or a different synthetic fiber or film.

2. A method for producing a shaped microporous, lightly crosslinked, water swellable, hydrogel polymer article which comprises the steps of:

A. producing an organic solvent solution of an isocyanato terminated prepolymer comprising the reaction product of:

i. poly(alkyleneoxy) polyol having an average molecular weight up to about 25,000, wherein the alkyleneoxy group contains from 2 to 4 carbon atoms, and ii. organic diisocyanate, wherein said poly(alkyleneoxy) polyol is a mixture of a major amount of a poly(ethyleneoxy) diol having an average molecular weight of from about 4,000 to about 25,000 and a minor amount of a higher polyol of the group poly(alkyleneoxy) triol or poly(alkyleneoxy) tetrol having from 2 to 4 carbon atoms in the alkyleneoxy group or aliphatic polyhydroxyl compound of the formula $C_nH_{2n+2-m}(OH)_m$ wherein n has a value of 3 to 6 and m has a value of 3 to 4 or mixture thereof, said triol or tetrol having an average molecular weight of from about 92 to 5,000, wherein the mole ratio of diol to higher polyol in said mixture is from about 6:1 to 40:1; and wherein the equivalents ratio of isocyanato groups to hydroxyl groups is from about 1.2:1 to about 1.6:1;

B. impregnating said isocyanato terminated prepolymer solution with a minor significant amount of a liquid nonsolvent;

C. extruding or spinning said impregnated isocyanato terminated solution into a crosslinking bath comprising:

i. a crosslinking agent for the isocyanato terminated prepolymer of the group (a) water or (b) organic polyamine, wherein said polyamine is a primary or secondary diamine or triamine and wherein the equivalents of reactive crosslinking groups in said crosslinking agent used is equivalent to the number of equivalents of isocyanato groups present in said prepolymer; and D. recovering the lightly crosslinked, water swellable, shaped microporous hydrogel article.

3. The method for producing a shaped microporous, water swellable, lightly crosslinked, hydrogel polymer article as claimed in claim 2, wherein said poly(alkyleneoxy) polyol is poly(ethyleneoxy) diol having an average molecular weight of from 4,000 to 25,000.

4. The method for producing a shaped microporous, water swellable, lightly crosslinked, hydrogel polymer article as claimed in claim 2, wherein said poly(alkyleneoxy) polyol is poly(alkyleneoxy) diol having an average molecular weight of from about 6,000 to 20,000.

5. The method for producing a shaped microporous, water swellable, lightly crosslinked, hydrogel polymer article as claimed in claim 2, wherein said poly(alkyleneoxy) polyol is a mixture of poly(ethyleneoxy) diol having an average molecular weight from about 6,000 to 20,000 and a poly(ethyleneoxy) triol having an average molecular weight of from about 500 to 1,500, wherein the mole ratio of diol to triol is from about 15:1 to about 30:1.

6. The method for producing a shaped microporous, water swellable, lightly crosslinked, hydrogel polymer article as claimed in claim 2, wherein said organic diisocyanate is methylenebis(4-phenylisocyanate).

7. The method for producing a shaped microporous, water swellable, lightly crosslinked, hydrogel polymer article as claimed in claim 3, wherein said organic diisocyanate is methylbis(4-phenylisocyanate).

8. The method for producing a shaped microporous, water swellable, lightly crosslinked, hydrogel polymer article as claimed in claim 4, wherein said organic diisocyanate is methylenebis(4-phenylisocyanate).

9. The method for producing a shaped microporous, water swellable, lightly crosslinked, hydrogel polymer article as claimed in claim 5, wherein said organic diisocyanate is methylenebis(4-phenylisocyanate).

10. The method for producing a shaped microporous, water swellable, lightly crosslinked, hydrogel polymer article as claimed in claim 2, wherein said crosslinking agent is water present in said coagulant bath at an concentration up to 0.05 N.

11. The method for producing a shaped microporous, water swellable, lightly crosslinked, hydrogel polymer article as claimed in claim 5, wherein said crosslinking agent is water present in said coagulant bath at an concentration up to 0.05 N.

12. The method for producing a shaped microporous water swellable, lightly crosslinked, hydrogel polymer article as claimed in claim 6, wherein said crosslinking agent is water present in said coagulant bath at an concentration up to 0.05 N.

13. The method for producing a shaped microporous, water swellable, lightly crosslinked, hydrogel polymer article as claimed in claim 9, wherein said crosslinking agent is water present in said coagulant bath at an concentration up to 0.05 N.

14. The method for producing a shaped microporous, water swellable, lightly crosslinked, hydrogel polymer article as claimed in claim 2, wherein said crosslinking is an organic diamine present in said coagulant bath at an concentration up to 0.05 N.

15. The method for producing a shaped microporous, water swellable, lightly crosslinked hydrogel polymer article as claimed in claim 2, wherein said crosslinking agent is ethylene diamine present in said coagulant bath at an concentration up to 0.05 N.

16. The method for producing a shaped microporous water swellable, lightly crosslinked, hydrogel polymer article as claimed in claim 5, wherein said crosslinking agent is ethylene diamine present in said coagulant bath at an concentration up to 0.05 N.

17. The method for producing a shaped microporous, water swellable, lightly crosslinked, hydrogel polymer article as claimed in claim 6, wherein said crosslinking agent is ethylene diamine present in said coagulant bath at an concentration up to 0.05 N.

18. The method for producing a shaped microporous water swellable, lightly crosslinked, hydrogel polymer article as claimed in claim 9, wherein said crosslinking agent is ethylene diamine present in said coagulant bath at an concentration up to 0.05 N.

19. The method for producing a shaped microporous, water swellable, lightly crosslinked, hydrogel polymer article as claimed in claim 2 wherein said crosslinking agent is a mixture of organic diamine and organic triamine present in said coagulant bath at a concentration up to 0.05 N.

20. The method for producing a shaped microporous, water swellable, lightly crosslinked, hydrogel polymer article as claimed in claim 3, wherein said crosslinking agent is a mixture of organic diamine and organic triamine present in said coagulant bath at a concentration up to 0.05 N.

21. The method for producing a shaped microporous, water swellable, lightly crosslinked, hydrogel polymer article as claimed in claim 4, wherein said crosslinking agent is a mixture of organic diamine and organic triamine present in said coagulant bath at a concentration up to 0.05 N.

22. The method for producing a shaped microporous, water swellable, lightly crosslinked, hydrogel polymer article as claimed in claim 5, wherein said crosslinking agent is a mixture of organic diamine and organic triamine present in said coagulant bath at a concentration up to 0.05 N.

23. The method for producing a shaped microporous, water swellable, lightly crosslinked, hydrogel polymer article as claimed in claim 8, wherein said crosslinking agent is a mixture of organic diamine and organic triamine present in said coagulant bath at a concentration up to 0.05 N.

24. The method for producing a shaped microporous, water swellable, lightly crosslinked, hydrogel polymer article as claimed in claim 2, wherein the crosslinking agent is a mixture of ethylene diamine and diethylene triamine present in said coagulant bath at a concentration up to 0.05 N.

25. The method for producing a shaped microporous, water swellable, lightly crosslinked, hydrogel polymer article as claimed in claim 3, wherein the crosslinking agent is a mixture of ethylene diamine and diethylene triamine present in said coagulant bath at a concentration up to 0.05 N.

26. The method for producing a shaped microporous, water swellable, lightly crosslinked, hydrogel polymer article as claimed in claim 4, wherein the crosslinking agent is a mixture of ethylene diamine and diethylene triamine present in said coagulant bath at a concentration up to 0.05 N.

27. The method for producing a shaped microporous, water swellable, lightly crosslinked hydrogel polymer article as claimed in claim 7, wherein the crosslinking agent is a mixture of ethylene diamine and diethylene triamine present in said coagulant bath at a concentration up to 0.05 N.

28. The method for producing a shaped microporous, water swellable, lightly crosslinked, hydrogel polymer article as claimed in claim 8, wherein the crosslinking agent is a mixture of ethylene diamine and diethylene triamine present in said coagulant bath at a concentration up to 0.05 N.

29. The method for producing a shaped microporous, water swellable, lightly crosslinked hydrogel polymer article as claimed in claim 2, wherein said poly(alkyleneoxy) polyol is poly(ethyleneoxy) diol, said organic diisocyanate is tolylene diisocyanate, and said crosslinker is a mixture of ethylene diamine and diethylene triamine present in said coagulant bath at a concentration up to 0.05 N.

30. The method for producing a shaped microporous, water swellable, lightly crosslinked, hydrogel polymer article as claimed in claim 2, wherein said poly(alkyleneoxy) polyol is poly(ethyleneoxy) diol, said organic diisocyanate is methylene bis(4-phenylisocyanate), and said crosslinker is a mixture of ethylene diamine and diethylene triamine present in said coagulant bath at a concentration up to 0.05 N.

31. The method for producing a shaped microporous, water swellable, lightly crosslinked, hydrogel polymer article as claimed in claim 2, wherein said poly(alkyleneoxy) polyol is a mixture of poly(ethyleneoxy) diol and poly(ethyleneoxy) triol, said organic diisocyanate is methylenebis(4-phenylisocyanate), and said crosslinker is water present in said coagulant bath at a concentration up to 0.05 N.

32. The method for producing a shaped microporous, lightly crosslinked, hydrogel polymer article as claimed in claim 2, wherein said poly(alkyleneoxy) polyol is a mixture of poly(ethyleneoxy) diol and poly(ethyleneoxy) triol, said organic diisocyanate is methylenebis(4-phenylisocyanate), and said crosslinker is ethylene diamine present in said coagulant bath at a concentration up to 0.05 N.

33. A shaped, microporous, water-swellable, lightly crosslinked, hydrogel polymer article, said article produced by the process of claim 2.

* * * * *

UNITED STATES PATENT OFFICE
CERTIFICATE OF CORRECTION

Patent No. 3,939,105  Dated February 17, 1976

Inventor(s) A. P. Jones et al

It is certified that error appears in the above-identified patent and that said Letters Patent are hereby corrected as shown below:

Column 4, line 9, the formula should read:

$$C_nH_{2n+2-m}(OH)_m$$

Column 5, line 38 the term "hydrogen" should read as ---hydrogel---.

Signed and Sealed this fourth Day of May 1976

[SEAL]

Attest:

RUTH C. MASON  
Attesting Officer

C. MARSHALL DANN  
Commissioner of Patents and Trademarks